US011890236B2

(12) United States Patent
Ta et al.

(10) Patent No.: US 11,890,236 B2
(45) Date of Patent: Feb. 6, 2024

(54) ENCLOSURES INCLUDING SYSTEMS AND METHODS THEREOF FOR ESTABLISHING A STERILE ENVIRONMENT FOR A MEDICAL PROCEDURE

(71) Applicant: Bard Access Systems, Inc., Salt Lake City, UT (US)

(72) Inventors: Teresa Ta, Murray, UT (US); Michael Davis, West Jordan, UT (US); Kyle G. Thornley, Farmington, UT (US); James D. Beal, South Jordan, UT (US); Daniel B. Blanchard, Bountiful, UT (US); Glade H. Howell, Draper, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 212 days.

(21) Appl. No.: 17/207,372

(22) Filed: Mar. 19, 2021

(65) Prior Publication Data

US 2021/0290465 A1    Sep. 23, 2021

Related U.S. Application Data

(60) Provisional application No. 62/992,062, filed on Mar. 19, 2020.

(51) Int. Cl.
*A61G 10/00* (2006.01)
*A61B 90/40* (2016.01)
(Continued)

(52) U.S. Cl.
CPC ............ *A61G 10/005* (2013.01); *A61B 42/10* (2016.02); *A61B 90/40* (2016.02); *A61G 10/023* (2013.01);
(Continued)

(58) Field of Classification Search
CPC .... A61M 21/0094; A62B 29/00; A62B 31/00; A61B 90/05; A61B 90/40; A61B 2090/401
See application file for complete search history.

(56) References Cited

U.S. PATENT DOCUMENTS 4,612,916 A    9/1986   Akers et al.
5,316,541 A    5/1994   Fischer
(Continued)

FOREIGN PATENT DOCUMENTS

WO       199420041 A1    9/1994
WO       2004024014 A1   3/2004
(Continued)

OTHER PUBLICATIONS

PCT/US2021/023268 filed Mar. 19, 2021 International Search Report and Written Opinion dated Jul. 14, 2021.

*Primary Examiner* — Thaddeus B Cox
(74) *Attorney, Agent, or Firm* — Rutan & Tucker LLP

(57) ABSTRACT

Disclosed are enclosures for establishing a sterile environment over a patient for a medical procedure, as well as systems and methods thereof. An enclosure can include an expandable portion of a barrier separating a sterile environment inside of the enclosure from a non-sterile environment outside of the enclosure and a patient-interfacing portion of the barrier. The enclosure can also include a support system coupled to the patient-interfacing portion of the barrier in some embodiments. The patient-interfacing portion of the barrier can include one or more fenestrations for placement directly over one or more areas of interest of the patient, as well as for access to the areas of interest from within the sterile environment. When present, the support system can flank the fenestration. The support system is configured to
(Continued)

support the enclosure on a surface when placed over an appendage of the patient or a main body of the patient.

25 Claims, 3 Drawing Sheets

(51) Int. Cl.
    *A61B 46/20*     (2016.01)
    *A61B 42/10*     (2016.01)
    *A61G 10/02*     (2006.01)

(52) U.S. Cl.
    CPC ... *A61B 2046/205* (2016.02); *A61B 2090/401* (2016.02)

(56) References Cited

U.S. PATENT DOCUMENTS

| | | | |
|---|---|---|---|
| 2002/0045796 | A1 | 4/2002 | O'Connor et al. |
| 2006/0021621 | A1* | 2/2006 | Kriek ............... A61B 42/10 128/849 |
| 2014/0163326 | A1* | 6/2014 | Forsell ............... A61B 90/40 600/207 |
| 2014/0316455 | A1* | 10/2014 | Gnanashanmugam ................. A61G 13/108 606/1 |
| 2016/0074268 | A1* | 3/2016 | Breegi ............... A61G 11/009 600/21 |
| 2022/0039908 | A1* | 2/2022 | Okajima ............ A61G 10/005 |

FOREIGN PATENT DOCUMENTS

| | | | |
|---|---|---|---|
| WO | 2014145032 A1 | 9/2014 | |
| WO | 2014189874 A1 | 11/2014 | |

\* cited by examiner

ENCLOSURES INCLUDING SYSTEMS AND METHODS THEREOF FOR ESTABLISHING A STERILE ENVIRONMENT FOR A MEDICAL PROCEDURE

PRIORITY

This application claims the benefit of priority to U.S. Provisional Application No. 62/992,062, filed Mar. 19, 2020, which is incorporated by reference in its entirety into this application.

BACKGROUND

Medical procedures such as surgical procedures require taking certain precautions to ensure the immediate environment in which the medical procedures are performed is sterile. Ensuring such an environment is sterile protects patients from infection when their natural protective barrier (i.e., their skin) is broken for the medical procedures.

Disclosed herein are enclosures for establishing a sterile environment over a patient for a medical procedure, as well as systems and methods thereof.

SUMMARY

Disclosed herein is an enclosure for establishing a sterile environment over a patient for a medical procedure. The enclosure includes, in some embodiments, an expandable portion of a barrier and a patient-interfacing portion of the barrier. The expandable portion of the barrier separates the sterile environment inside of the enclosure from a non-sterile environment outside of the enclosure. The expandable portion of the barrier is configured to expand from an unexpanded state to an expanded state for working within the sterile environment. The patient-interfacing portion of the barrier includes a fenestration configured for placement directly over an area of interest of a patient. The fenestration has a sealed state and an unsealed state for access to the area of interest from within the sterile environment.

In some embodiments, the enclosure further includes a support system coupled to the patient-interfacing portion of the barrier flanking the fenestration. The support system is configured to support the enclosure on a surface when placed over an appendage of the patient or a main body of the patient. The patient can be positioned in any one of a number of anatomical positions on the surface.

In some embodiments, the support system is configured to expand from an unexpanded state to an expanded state in concert with the expandable portion of the barrier.

In some embodiments, the support system is configured to expand from an unexpanded state to an expanded state independent of the expandable portion of the barrier.

In some embodiments, the enclosure further includes a pair of framed ends of the enclosure configured to support the expandable portion of the barrier. Each framed end of the pair of framed ends is configured to lie down on the patient-interfacing portion of the barrier in the unexpanded state of the barrier. Each framed end of the pair of framed ends is also configured to extend vertically from the patient-interfacing portion of the barrier in the expanded state of the barrier.

In some embodiments, the enclosure further includes an air inlet fluidly connected to the inside of the enclosure. The air inlet is configured for introducing filtered air into the inside of the enclosure for inflating the expandable portion of the barrier from the unexpanded state to the expanded state or maintaining a greater pressure inside of the enclosure than outside of the enclosure.

In some embodiments, the enclosure further includes an inline high-efficiency particulate-arresting ("HEPA") air filter optionally including an antimicrobial coating on a filter medium of the HEPA air filter. The HEPA air filter is configured to prevent microbial contamination of the sterile environment inside of the enclosure.

In some embodiments, the fenestration includes an outer seal over a patient-interfacing surface of the patient-interfacing portion of the barrier in the sealed state of the fenestration.

In some embodiments, a perimeter of the patient-interfacing surface of the patient-interfacing portion of the barrier around the fenestration includes an adhesive. The adhesive is configured to adhere the patient-interfacing portion of the barrier to the patient with the perimeter of the fenestration around the area of interest subsequent to sterilization thereof. The outer seal of the fenestration is configured to protect and maintain an integrity of the adhesive prior to use.

In some embodiments, the fenestration includes an inner seal over an inner surface of the patient-interfacing portion of the barrier in the sealed state of the fenestration. The inner seal of the fenestration is configured to be removed subsequent to adhering the patient-interfacing portion of the barrier to the patient. Removing the inner seal subsequent to adhering the patient-interfacing portion of the barrier to the patient maintains the sterile environment over the patient.

In some embodiments, the enclosure further includes one or more pairs of long-sleeved gloves integrated into the expandable portion of the barrier. The long-sleeved gloves are configured to be worn by a clinician when performing the medical procedure within the sterile environment.

In some embodiments, the enclosure further includes one or more closed-ended tubes integrated into the expandable portion of the barrier. The one-or-more closed-ended tubes are configured to accept insertion of a probe for use during the medical procedure within the sterile environment.

In some embodiments, the enclosure further includes one or more pockets integrated into the expandable portion of the barrier. The one-or-more pockets are configured to hold procedural equipment or supplies for the medical procedure. The one-or-more pockets are inside of the enclosure, outside of the enclosure, or a combination thereof.

In some embodiments, the enclosure further includes an introducing means for introducing additional procedural equipment or supplies into the sterile environment inside of the enclosure from the non-sterile environment outside of the enclosure.

Also disclosed herein is a system for establishing a sterile environment over a patient for a medical procedure. The system includes, in some embodiments, an enclosure for placement over a patient and procedural equipment or supplies for the medical procedure in a sterile environment inside of the enclosure. The enclosure includes, in some embodiments, an expandable portion of a barrier and a patient-interfacing portion of the barrier. The expandable portion of the barrier separates the sterile environment inside of the enclosure from a non-sterile environment outside of the enclosure. The expandable portion of the barrier is configured to expand from an unexpanded state to an expanded state for working within the sterile environment. The patient-interfacing portion of the barrier includes a fenestration configured for placement directly over an area of interest of a patient. The fenestration has a sealed state and an unsealed state for access to the area of interest from within the sterile environment.

In some embodiments, the enclosure further includes a support system coupled to the patient-interfacing portion of the barrier flanking the fenestration. The support system is configured to support the enclosure on a surface when placed over an appendage of the patient or a main body of the patient. The patient can be positioned in any one of a number of anatomical positions on the surface.

In some embodiments, the fenestration includes an outer seal over a patient-interfacing surface of the patient-interfacing portion of the barrier in the sealed state of the fenestration.

In some embodiments, a perimeter of the patient-interfacing surface of the patient-interfacing portion of the barrier around the fenestration includes an adhesive. The adhesive is configured to adhere the patient-interfacing portion of the barrier to the patient with the perimeter of the fenestration around the area of interest subsequent to sterilization thereof. The outer seal of the fenestration is configured to protect and maintain an integrity of the adhesive prior to use.

In some embodiments, the fenestration includes an inner seal over an inner surface of the patient-interfacing portion of the barrier in the sealed state of the fenestration. The inner seal of the fenestration is configured to be removed subsequent to adhering the patient-interfacing portion of the barrier to the patient. Removing the inner seal subsequent to adhering the patient-interfacing portion of the barrier to the patient maintains the sterile environment over the patient.

In some embodiments, the procedural equipment includes one or more puncturing devices, one or more guidewires selected from access guidewires, maneuver guidewires, and rail guidewires, one or more catheters, one or more syringes, or a combination thereof.

In some embodiments, the supplies include one or packages of an antiseptic, saline, or a medicament, one or more swabs, gauze, one or more drapes, or a combination thereof.

Also disclosed herein is a method of a system for establishing a sterile environment over a patient for a medical procedure. The method includes, in some embodiments, a placing step, an expanding step, and a working step. The placing step includes placing an enclosure over an appendage of a patient or a main body of the patient such that a fenestration of a patient-interfacing portion of a barrier of the enclosure is directly over an area of interest of the patient. The expanding step includes expanding an expandable portion of the barrier separating a sterile environment inside of the enclosure from a non-sterile environment outside of the enclosure from an unexpanded state to an expanded state. The working step includes working in the sterile environment to perform the medical procedure.

In some embodiments, the expanding step includes lifting each framed end of a pair of framed ends of the enclosure from the patient-interfacing portion of the barrier in the unexpanded state of the expandable portion of the barrier to form the expanded state thereof.

In some embodiments, the expanding step includes introducing filtered air into the inside of the enclosure with an air inlet fluidly connected to the inside of the enclosure.

In some embodiments, introducing the filtered air into the inside of the enclosure with the air inlet also introduces the filtered air into a support system coupled to the patient-interfacing portion of the barrier that flanks both the fenestration and the appendage or main body of the patient. Introducing the filtered air into the support system expands the support system from an unexpanded state to an expanded state in concert with the expandable portion of the barrier.

In some embodiments, the method further includes a first removing step and an adhering step. The first removing step includes removing an outer seal of the fenestration from a patient-interfacing surface of the patient-interfacing portion of the barrier. The first removing step exposes a perimeter around the fenestration having an adhesive on the patient-interfacing surface. The adhering step includes adhering the patient-interfacing portion of the barrier to the patient with the perimeter of the fenestration around the area of interest.

In some embodiments, the method further includes a second removing step of removing an inner seal of the fenestration from an inner surface of the patient-interfacing portion of the barrier after adhering the patient-interfacing portion of the barrier to the patient. The second removing step maintains the sterile environment over the patient.

These and other features of the concepts provided herein will become more apparent to those of skill in the art in view of the accompanying drawings and following description, which describe particular embodiments of such concepts in greater detail.

DRAWINGS

DESCRIPTION

Figure 1:
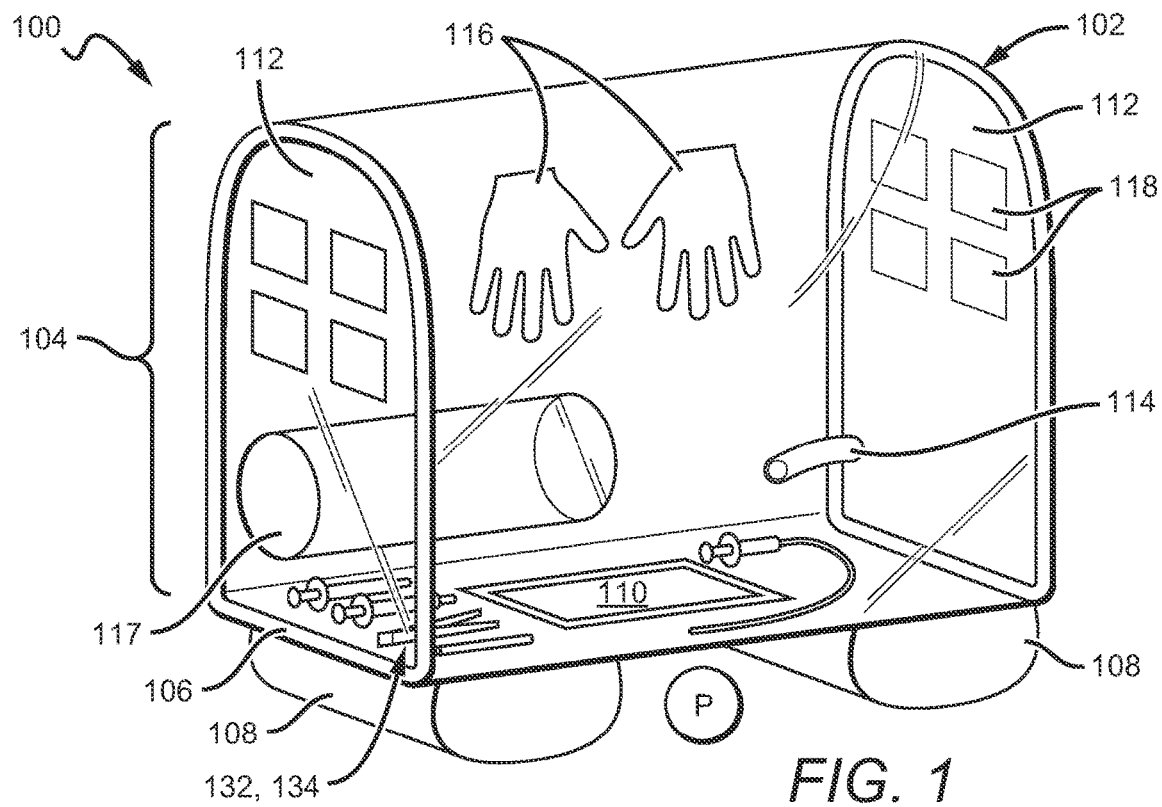
FIG. 1 illustrates a system including an enclosure for establishing a sterile environment in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Enclosures for Establishing a Sterile Environment

FIG. 1 illustrates a system 100 including an enclosure 102 for establishing a sterile environment in accordance with some embodiments. While FIG. 1 shows a system including the enclosure 102 for establishing a sterile environment, the enclosure 102 will be primarily described in this section. Systems for establishing a sterile environment are primarily described in more detail below in the section on such systems.

The enclosure 102 is configured for establishing a sterile environment over a patient for a medical procedure. The enclosure 102 can be of any size suitable for the medical procedure.

As shown, the enclosure 102 includes a barrier formed of an expandable portion 104 of the barrier and a patient-interfacing portion 106 of the barrier. The barrier separates the sterile environment inside of the enclosure 102 from a non-sterile environment outside of the enclosure 102. As such, each portion of the expandable portion 104 and the patient-interfacing portion 106 of the barrier separates the sterile environment inside of the enclosure 102 from a non-sterile environment outside of the enclosure 102.

The expandable portion 104 of the barrier is configured to expand from an unexpanded state of the expandable portion 104 to an expanded state for working within the sterile environment. The expandable portion 104 can be an inflatable bag of a translucent plastic (e.g., polyethylene, styrene, polycarbonate, etc.) over the patient-interfacing portion 106 of the barrier or a framed structure including the translucent plastic stretched between frame elements.

With respect to the framed structure, for example, the framed structure can include a pair of framed ends 112 of the enclosure 102 configured to support the expandable portion 104 of the barrier. Each framed end of the pair of framed ends 112 is configured to lie down on the patient-interfacing portion 106 of the barrier in the unexpanded state of the barrier. Each framed end of the pair of framed ends 112 is also configured to extend vertically from the patient-interfacing portion 106 of the barrier in the expanded state of the barrier. Each framed end of the pair of framed ends can be independently lifted from the patient-interfacing portion 106 of the barrier in the unexpanded state of the expandable portion 104 of the barrier to form the expanded state thereof with simultaneous introduction of filtered air commensurate with a rate at which the pair of framed ends are lifted from the patient-interfacing portion 106 of the barrier. Alternatively, the framed structure is inflated by introduction of the filtered air.

In view of the foregoing, the enclosure 102 can further include an air inlet 114 fluidly connected to the inside of the enclosure 102. The air inlet 114 is configured for introducing air (e.g., filtered air) into the inside of the enclosure 102 for expanding the enclosure 102 from the unexpanded state of the expandable portion 104 to the expanded state thereof. For example, the air inlet is configured for equilibrating pressure inside of the enclosure 102 when expanding the expandable portion 104 of the framed structure set forth above from the unexpanded state to the expanded state thereof. And, for example, the air inlet is configured for inflating the expandable portion 104 of the inflatable bag set forth above from the unexpanded state to the expanded state thereof. In addition, the air inlet 114 is configured for introducing air (e.g., filtered air) into the inside of the enclosure 102 for maintaining a greater pressure inside of the enclosure 102 than outside of the enclosure 102 when needed. The air inlet 114 can be fluidly connected to a pump for inflating the expandable portion 104 of the barrier or maintaining the greater pressure inside of the enclosure 102 than outside of the enclosure 102.

It should be understood that whether the expandable portion 104 of the barrier includes the inflatable bag or the framed structure, the expandable portion 104 of the barrier can be inflated through the air inlet 114. In addition, maintaining a greater pressure inside of the enclosure 102 than outside of the enclosure 102 is particularly important in maintaining the structural integrity of the expandable portion 104 of the barrier when the expandable portion 104 is the inflatable bag.

To provide filtered air into the inside of the enclosure 102, the enclosure can further include an inline HEPA air filter optionally including an antimicrobial coating on a filter medium of the HEPA air filter. The HEPA air filter is configured to prevent microbial contamination of the sterile environment inside of the enclosure 102.

The patient-interfacing portion 106 of the barrier includes a fenestration 110 configured for placement directly over an area of interest (e.g., surgical area, wound such as an open wound, a previously closed and dressed wound, a burn wound, etc.) of a patient P; however, the patient-interfacing portion 106 of the barrier is not limited to the fenestration 110. Indeed, the patient-interfacing portion 106 of the barrier can include any number of additional fenestrations to the fenestration 110. The fenestration 110 has a sealed state and an unsealed state for access to the area of interest from within the sterile environment.

The fenestration 110 includes an outer seal over a patient-interfacing surface (e.g., outer surface) of the patient-interfacing portion 106 of the barrier in the sealed state of the fenestration 110. A perimeter of the patient-interfacing surface around the fenestration 110 includes an adhesive configured to adhere the patient-interfacing portion 106 of the barrier to the patient P with the perimeter of the fenestration 110 around the area of interest subsequent to sterilization thereof. The outer seal of the fenestration 110 is configured to protect and maintain an integrity of the adhesive prior to use.

The fenestration 110 also includes an inner seal over an inner surface of the patient-interfacing portion 106 of the barrier in the sealed state of the fenestration 110. The inner seal of the fenestration 110 is configured to be removed subsequent to adhering the patient-interfacing portion 106 of the barrier to the patient P. Removing the inner seal subsequent to adhering the patient-interfacing portion 106 of the barrier to the patient maintains the sterile environment over the patient P by stopping unfiltered air from entering the enclosure 102 through the fenestration 110.

As shown, the enclosure 102 can further include a support system 108 coupled to the patient-interfacing portion 106 of the barrier. When present, the support system 108 is coupled to the patient-interfacing portion 106 of the barrier and includes at least a pair of supports flanking the fenestration 110. The support system 108 is configured to support the enclosure 102 on a surface (e.g., a top of an operating table, a top of a bed, etc.) when placed over an appendage of the patient P or a main body of the patient P such that the supports flank the appendage or main body of the patient P. The patient P can be positioned in any one of a number of anatomical positions (e.g., supine, prone, right lateral recumbent, left lateral recumbent, etc.) on the surface for use with the enclosure 102.

The support system 108 can be immediately ready to be placed over the patient P subsequent to unpackaging the enclosure 102 or the support system 108 can be configured to expand from an unexpanded state to an expanded state for use with the patient P. With respect to the former, for example, the supports of support system 108 can include fiberfill stuffing, thereby making the support system 108 immediately ready to be placed over the patient subsequent to unpackaging. With respect to the latter, for example, the support system 108 can be configured to expand from the unexpanded state to the expanded state in concert with the expandable portion 104 of the barrier. That is, the supports of the support system 108 can be fluidly connected to the inside of the enclosure 102 such that when the expandable portion 104 of the barrier is inflated, the support system 108 is also inflated. Alternatively, the support system 108 can be configured to expand from the unexpanded state to the expanded state independent of the expandable portion 104 of the barrier through one or more inlets exclusive to the support system 108. In this way, the supports of the support system 108 can be expanded from the unexpanded state to the expanded state with a different fluid than the expandable portion 104 of the barrier. Instead of air, for example, water can be used to expand the support system 108 from the unexpanded state to the expanded state. Water is advantageous in that it provides more weight to the enclosure 102 than air and lowers a center of gravity of the enclosure 102 as well.

The enclosure 102 can further include one or more pairs of long-sleeved gloves 116 integrated into the translucent plastic of the expandable portion 104 of the barrier. The one-or-more pairs of long-sleeved gloves 116 are configured to be worn by a clinician when performing the medical procedure within the sterile environment of the enclosure 102.

The enclosure 102 can further include one or more closed-ended tubes 117 integrated into translucent plastic of the expandable portion of the barrier. Instead of being configured with fingertips like the one-or-more long-sleeved gloves, the one-or-more closed-ended tubes 117 are configured to accept insertion of a probe (e.g., an ultrasound probe) for use during the medical procedure within the sterile environment of the enclosure 102.

The enclosure 102 can further include one or more pockets 118 integrated into the expandable portion 104 or the patient-facing portion 106 of the barrier. When present, the one-or-more pockets 118 are configured to hold procedural equipment or supplies for the medical procedure. The one-or-more pockets 118 are also configured to hold the procedural equipment or supplies subsequent to the use thereof during the medical procedure, thereby safely keeping biohazardous waste safely contained in the enclosure 102. The one-or-more pockets 118 can be inside of the enclosure 102, outside of the enclosure 102, or a combination thereof. Additionally or alternatively, the enclosure 102 can include loops, clamps, hook-and-loop fasteners, snaps, glue dots, or other fastening devices to hold the procedural equipment or supplies for the medical procedure. The enclosure 102 can further include one or more rigid trays configured to hold the procedural equipment or supplies for the medical procedure. Such rigid trays can include any of the foregoing fastening devices for holding the procedural equipment, and the enclosure 102, in turn, can include any of the foregoing fastening devices for holding the rigid trays.

The enclosure 102 can further include an introducing means for introducing procedural equipment or supplies into the sterile environment inside of the enclosure 102 from the non-sterile environment outside of the enclosure.

Figure 2:
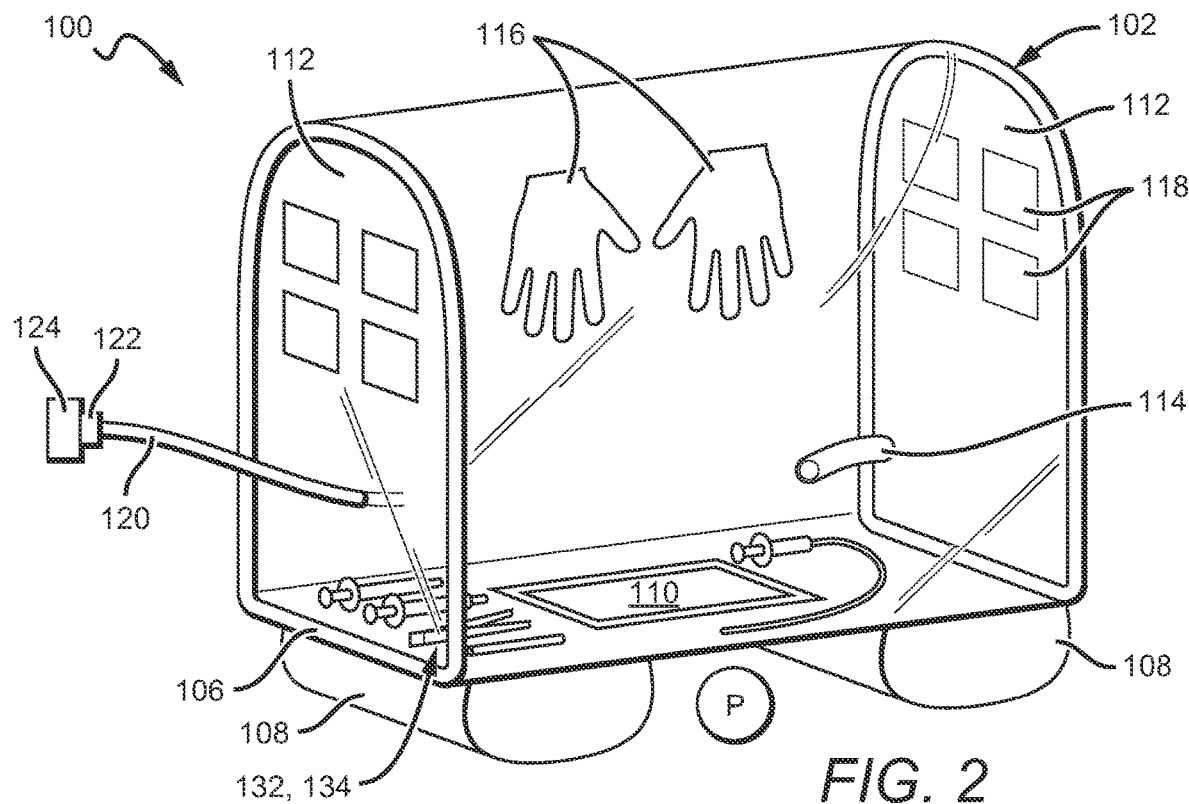
FIG. 2 illustrates the system of FIG. 1 including an enclosure with a barrier-crossing tube in accordance with some embodiments.

FIG. 2 illustrates the system 100 of FIG. 1 including the enclosure 102 with a barrier-crossing tube 120 in accordance with some embodiments. While the tube 120 is shown crossing the barrier of a framed end of the pair of framed ends 112 of the enclosure 102, the tube 120 can cross any portion of the barrier that separates the sterile environment inside of the enclosure 102 from a non-sterile environment outside of the enclosure 102. The tube 120 can include a Luer connector 122 and a cap 124 configured to maintain a sterility of a lumen of the tube 120 for introducing supplies into the sterile environment inside of the enclosure 102 such as a guidewire, saline, a solution including a medicament, or the like.

Figure 3:
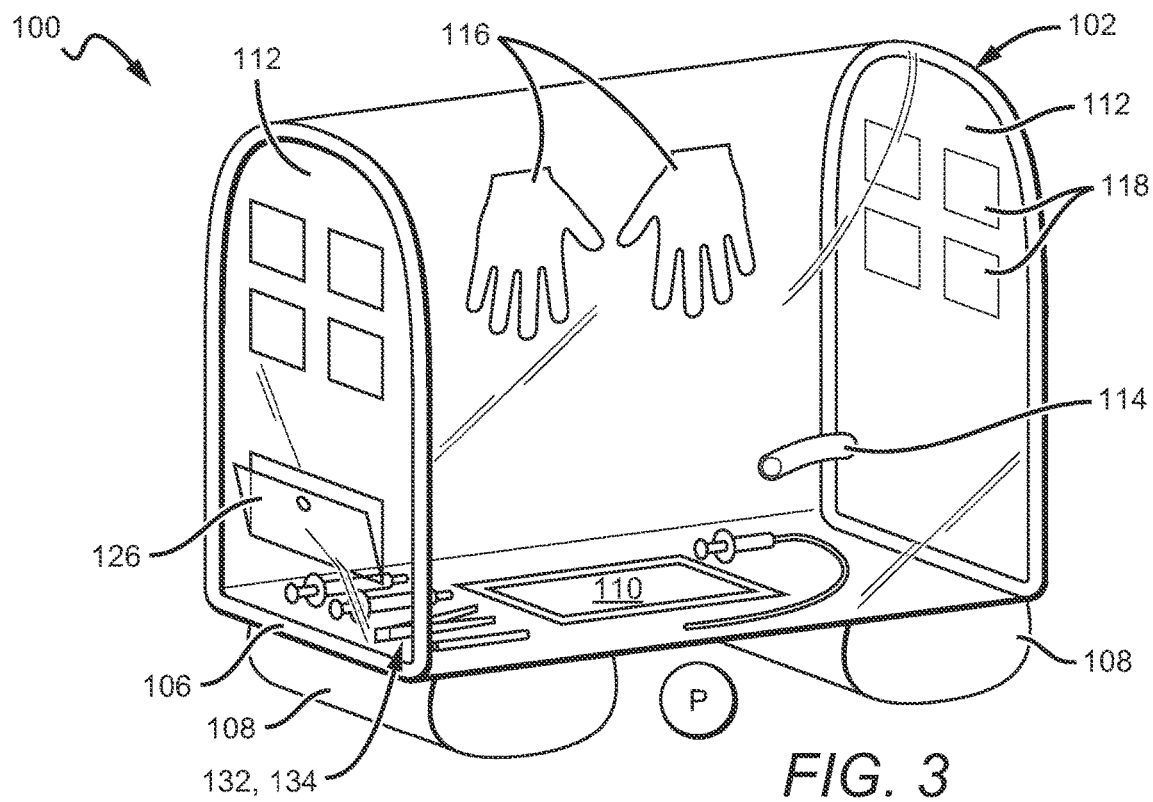
FIG. 3 illustrates the system of FIG. 1 including an enclosure with a door in accordance with some embodiments.

FIG. 3 illustrates the system 100 of FIG. 1 including the enclosure 102 with a door 126 in accordance with some embodiments. While the door 126 is shown in the barrier of a framed end of the pair of framed ends 112 of the enclosure 102, the door 126 can be in any portion of the barrier that separates the sterile environment inside of the enclosure 102 from a non-sterile environment outside of the enclosure 102. The door 126 can include a knob, hook, or the like on one side or both sides of the door 126 configured to facilitate opening the door 126 for introducing the procedural equipment or supplies into the sterile environment inside of the enclosure 102 and closing the door 126 thereafter.

Figure 4:
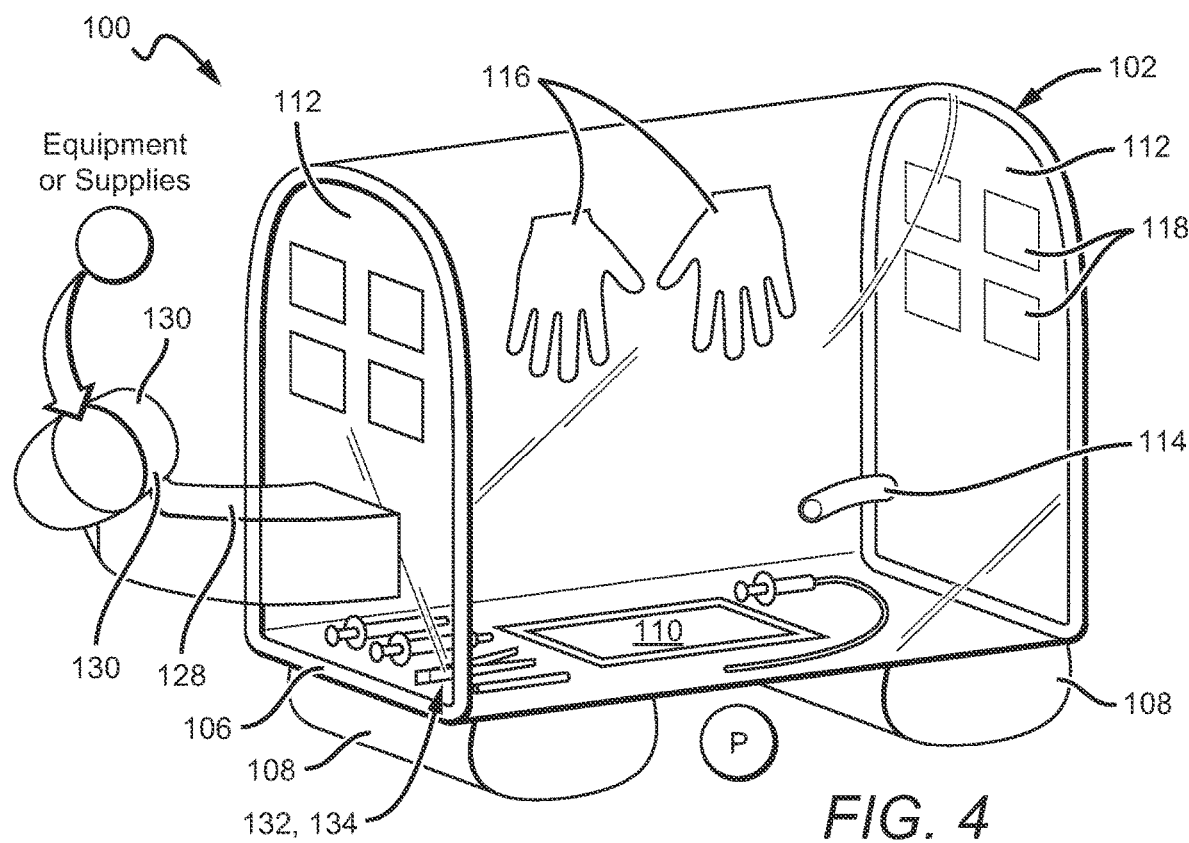
FIG. 4 illustrates the system of FIG. 1 including an enclosure with a chute in accordance with some embodiments.

FIG. 4 illustrates the system 100 of FIG. 1 including the enclosure 102 with a chute 128 in accordance with some embodiments. While the chute 128 is shown extending from the barrier of a framed end of the pair of framed ends 112 of the enclosure 102, the chute 128 can be extend from any portion of the barrier that separates the sterile environment inside of the enclosure 102 from a non-sterile environment outside of the enclosure 102. The chute 128 can include a fold-top end having one or more flaps 130 configured to fold over the chute 128 in a closed state of the chute 128. The one-or-more flaps 130 are configured to open to one or more sides of the chute 128 for an open state of the chute 128 for introducing the procedural equipment or supplies into the sterile environment inside of the enclosure 102. The one-or-more flaps 130 can include a sterile side corresponding to an inside of the chute 128 when in the closed state thereof. Handling the one-or-more flaps 130 only by a non-sterile side of the one-or-more flaps 130 opposite the sterile side ensures the procedural equipment or supplies dropped into the chute 128 do not come into contact with a non-sterile surface such as the non-sterile side of the one-or-more flaps 130.

The chute 128 can be formed from any tube of the one-or-more closed-ended tubes set forth above configured to accept insertion of a probe (e.g., an ultrasound probe) for use during the medical procedure within the sterile environment of the enclosure 102. Indeed, such closed-ended tubes can have scores or similar weakened areas that can be broken apart to create the fold-top end having the one-or-more flaps 130.

Figure 5:
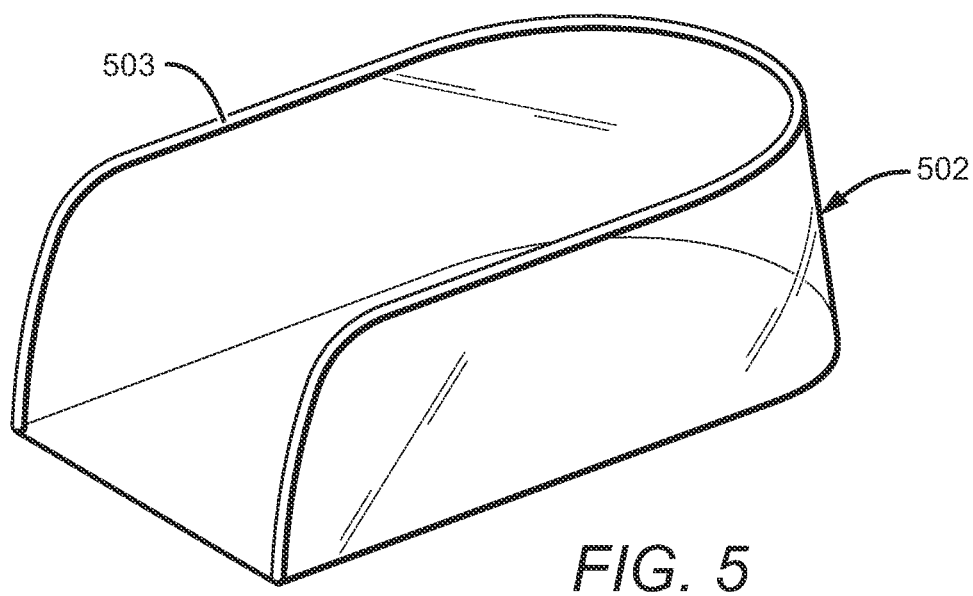
FIG. 5 illustrates an alternative enclosure for the system of FIG. 1 in accordance with some embodiments.

FIG. 5 illustrates an alternative enclosure 502 for the system 100 of FIG. 1 in accordance with some embodiments. Like the enclosure 102 of any of FIGS. 1-4, the enclosure 502 is configured for establishing a sterile environment over a patient for a medical procedure. The enclosure 502 is a framed structure like that set forth above for the enclosure 102; however, the enclosure 502 includes a pop-up frame 503 including the translucent plastic stretched between portions of the pop-up frame 503.

The enclosure 502 is configured with an unexpanded state in which the pop-up frame 503 is twisted and folded upon itself in one or more revolutions of the pop-up frame 503, thereby locking an amount of torsional potential energy into the pop-up frame 503 in the unexpanded state of the enclosure 502. The enclosure 502 is also configured with an expanded state in which the pop-up frame 503 is untwisted and unfolded. A transition from the unexpanded state to the expanded state of the enclosure 502 is effectuated by releasing the torsional potential energy in the pop-up frame 503 by perturbing an energetic state of the pop-up frame 503 at a local minimum in the unexpanded state or by unclipping one or more clips that clip together the one-or-more revolutions of the pop-up frame 503 in the unexpanded state.

While not shown, the enclosure 502 includes one or more features set forth above for the enclosure 102 selected from at least the air inlet 114, the fenestration 110, the one-or-more pairs of long-sleeved gloves 116, the one-or-more closed-ended tubes 117, the one-or-more pockets 118, and the introducing means for introducing procedural equipment or supplies into the sterile environment inside of the enclosure 502.

Figure 6:
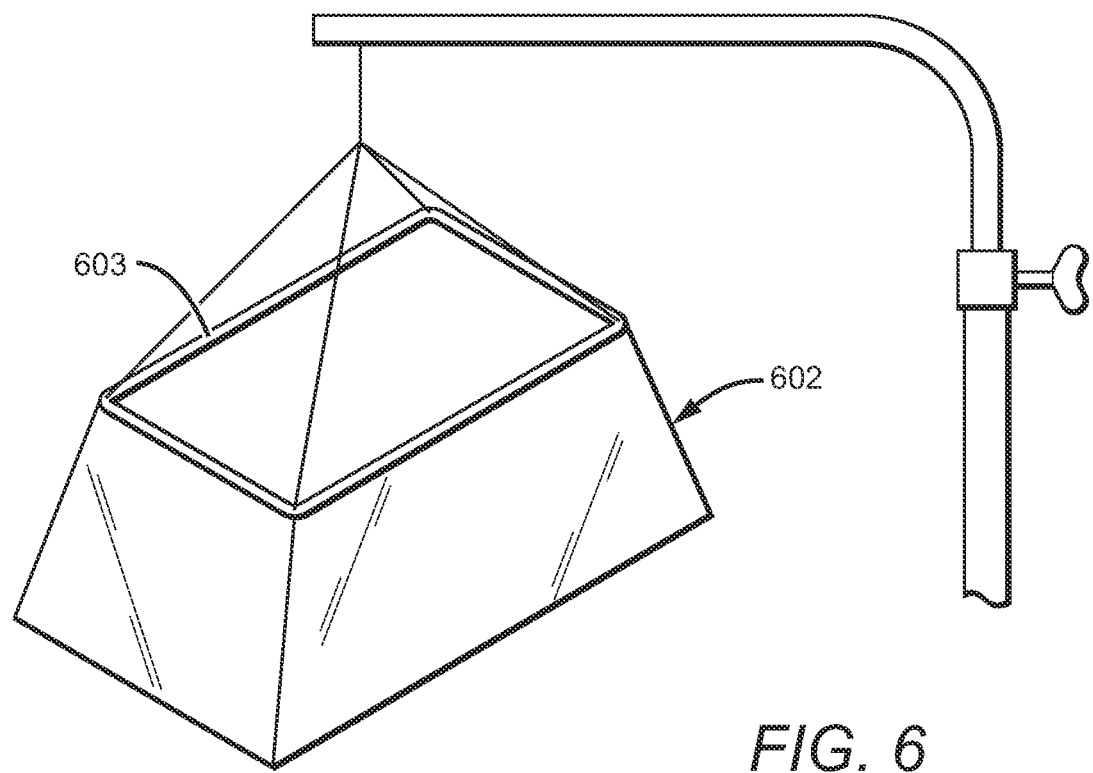
FIG. 6 illustrates another alternative enclosure for the system of FIG. 1 in accordance with some embodiments.

FIG. 6 illustrates the system of FIG. 1 with another alternative enclosure in accordance with some embodiments.

Like the enclosure 102 of any figure of FIGS. 1-4, the enclosure 602 is configured for establishing a sterile environment over a patient for a medical procedure. The enclosure 602 is a framed structure like that set forth above for the enclosure 102; however, the enclosure 602 includes a top frame 603 including the translucent plastic stretched between portions of the top frame 603, as well as translucent plastic hanging from the top frame 603. That said, the enclosure 602 is not limited to the top frame 603. Indeed, the enclosure 602 can further include a bottom frame framing a patient-interfacing portion like that of the enclosure 102 or even framed ends like the pair of framed ends 112 of the enclosure 102.

The enclosure 602 is configured with an unexpanded state in which the translucent plastic attached to the top frame 603 is folded into the enclosure 602 or bunched up under the top frame 603. The enclosure 602 is also configured with an expanded state in which the translucent plastic attached to the top frame 603 hangs from the top frame 603. A transition from the unexpanded state to the expanded state of the enclosure 602 is effectuated by hanging the enclosure 602 on a boom or the like by the top frame 603 using a cord.

While not shown, the enclosure 602 includes one or more features set forth above for the enclosure 102 selected from at least the air inlet 114, the fenestration 110, the one-or-more pairs of long-sleeved gloves 116, the one-or-more closed-ended tubes 117, the one-or-more pockets 118, and the introducing means for introducing procedural equipment or supplies into the sterile environment inside of the enclosure 602.

Systems for Establishing a Sterile Environment

FIG. 1 illustrates the system 100 including the enclosure 102 for establishing a sterile environment in accordance with some embodiments. While the system 100 set forth below is described with reference to the enclosure 102, it should be understood the system 100 can alternatively include the enclosure 502 or 602.

As shown, the system 100 includes the enclosure 102 for placement over the patient P, as well as sterile procedural equipment 132 or supplies 134 for the medical procedure in the sterile environment inside of the enclosure 102.

The enclosure 102 is primarily described in the foregoing section.

The procedural equipment 132 or supplies 134 for the medical procedure can be selected for any medical procedure of a number of medical procedures such as a medical procedure for placing a central venous catheter ("CVC"), a peripherally inserted central catheter ("PICC"), a medical port, or the like. With respect to the procedural equipment 132, the procedural equipment 132 can include without limitation one or more puncturing devices, one or more guidewires selected from access guidewires, maneuver guidewires, and rail guidewires, one or more catheters (e.g., a CVC, a PICC, etc.), one or more syringes, or a combination thereof. With respect to the supplies 134, the supplies 134 can include without limitation one or more packages of an antiseptic (e.g., iodopovidone), saline, or a medicament, one or more swabs, gauze, or a combination thereof.

The system 100 can further include packaging such as a bag or pouch, additional supplies such as one or more pairs of gloves or those selected from the supplies 134 for the medical procedure, instructions for use, manufacturing information, or the like. For example, the enclosure 102 including the procedural equipment 132 or supplies 134 inside the enclosure 102 can be disposed in the bag or pouch in the unexpanded state of the enclosure 102. In addition, the additional supplies such as the one-or-more pairs of gloves, one or more packages of antiseptic, or the like can be disposed in the bag or pouch along with the enclosure 102 for independently removing the additional supplies to prepare the patient P and the area or interest for the medical procedure before placing the enclosure 102 and the fenestration 110 thereof over the area of interest. The bag or pouch can be sterilized with ethylene-oxide gas and sealed with the enclosure 102 and the additional supplies, thereby forming the system 100 in accordance with some embodiments. Such a system can be shipped or stored until ready to use.

Advantageously, the system 100 obviates a need for a clinician performing a medical procedure with the system 100 to don protective equipment such as a gown or mask or even use one or more drapes to set-up a sterile field. As such, the system 100 saves time and money, as well decrease the possibility for compromising a sterile field.

Methods

Methods of the system 100 include methods for establishing a sterile environment over the patient P for a medical procedure.

A method for establishing a sterile environment over the patient P for a medical procedure includes at least a placing step, an expanding step, and a working step in association with the system 100 as set forth in more detail below.

The placing step includes placing the enclosure 102 over an appendage of the patient P or the main body of the patient P such that the fenestration 110 of the patient-interfacing portion 106 of the barrier is directly over an area of interest of the patient P. When the support system 108 is coupled to the patient-interfacing portion 106 of the barrier, the placing step also includes placing the support system 108 such that the fenestration-flanking supports of the support system 108 also flank the appendage or main body of the patient P.

The expanding step includes expanding the expandable portion 104 of the barrier separating the sterile environment inside of the enclosure 102 from the non-sterile environment outside of the enclosure 102 from the unexpanded state to the expanded state. The expanding step can be before or after the placing step.

Expanding the expandable portion 104 of the barrier can include lifting each framed end of the pair of framed ends 112 of the enclosure 102 from the patient-interfacing portion 106 of the barrier in the unexpanded state of the expandable portion 104 of the barrier to form the expanded state thereof. Simultaneously, filtered air can be introduced into the inside of the enclosure 102 with the air inlet 114 fluidly connected to the inside of the enclosure 102. Alternatively, such as in embodiments in which the expandable portion 104 of the barrier is an inflatable bag, but not limited thereto, the expanding step can include merely inflating the expandable portion 104 of the barrier with the filtered air introduced into the inside of the enclosure 102 with the air inlet 114. During the expanding step, any fenestrations (e.g., the fenestration 110) or other openings should remain sealed such that only filtered air is introduced into the inside of the enclosure 102.

As set forth above, introducing the filtered air into the inside of the enclosure 102 with the air inlet 114 can also introduce the filtered air into the support system 108 when the supports of the support system 108 are fluidly connected to the inside of the enclosure 102. In such embodiments, introducing the filtered air into the support system 108 expands the support system from the unexpanded state to the expanded state in concert with the expandable portion 104 of the barrier. That said, the support system 108 can be alternatively configured to expand from the unexpanded state to the expanded state independent of the expandable portion 104 of the barrier through one or more inlets exclusive to the support system 108. When the enclosure is so configured, the method can include a second expanding step before or after the foregoing expanding step of expanding the supports of the support system 108 from the unexpanded state to the expanded state with a same fluid (e.g., filtered air) or a different fluid (e.g., water) than that for the expandable portion 104 of the barrier.

The working step includes working in the sterile environment to perform the medical procedure.

The method can further include a preparing step of preparing the area of interest with an antiseptic before the placing step.

The method can further include a first removing step followed by an adhering step as set forth in more detail below. The first removing step can be performed at any time relative to the preparing step, but the adhering step is performed after the preparing step in order to maintain sterility.

The first removing step includes removing the outer seal of the fenestration 110 from the patient-interfacing surface of the patient-interfacing portion 106 of the barrier. The first removing step exposes the perimeter around the fenestration 110 having the adhesive on the patient-interfacing surface.

The adhering step includes adhering the patient-interfacing portion 106 of the barrier to the patient P by way of the adhesive exposed during the first removing step such that the perimeter of the fenestration 110 is around the area of interest.

The method can further include an inserting step of inserting at least one hand into a glove of the one-or-more pairs of long-sleeved gloves 116 integrated into the expandable portion 104 of the barrier followed by a second removing step of removing the inner seal of the fenestration 110 from the inner surface of the patient-interfacing portion 106 of the barrier. The second removing step should be after adhering the patient-interfacing portion 106 of the barrier to the patient to maintain the sterile environment over the patient P.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An enclosure for establishing a sterile environment over a patient for a medical procedure, comprising:
   an expandable portion of a barrier separating the sterile environment inside of the enclosure from a non-sterile environment outside of the enclosure, the expandable portion of the barrier configured to expand from an unexpanded state to an expanded state for working within the sterile environment;
   a patient-interfacing portion of the barrier including a fenestration configured for placement directly over an area of interest of the patient, the fenestration having a sealed state and an unsealed state for access to the area of interest from within the sterile environment; and
   a support system coupled to the patient-interfacing portion of the barrier flanking the fenestration, the support system configured to support the enclosure on a surface when the patient-interfacing portion is placed over an appendage of the patient or a main body of the patient, the patient positioned on the surface in any one of a number of anatomical positions.

2. The enclosure of claim 1, wherein the support system is configured to expand from the unexpanded state to the expanded state in concert with the expandable portion of the barrier.

3. The enclosure of claim 1, wherein the support system is configured to expand from the unexpanded state to the expanded state independent of the expandable portion of the barrier.

4. The enclosure of claim 1, further comprising a pair of framed ends of the enclosure configured to support the expandable portion of the barrier, each framed end of the pair of framed ends configured to lie down on the patient-interfacing portion of the barrier in the unexpanded state of the barrier and extend vertically from the patient-interfacing portion of the barrier in the expanded state of the barrier.

5. The enclosure of claim 1, further comprising an air inlet fluidly connected to an inside of the enclosure configured for introducing filtered air thereto for inflating the expandable portion of the barrier from the unexpanded state to the expanded state or maintaining a greater pressure inside of the enclosure than outside of the enclosure.

6. The enclosure of claim 5, further comprising an inline high-efficiency particulate-arresting ("HEPA") air filter including an optional antimicrobial coating on a filter medium of the HEPA air filter, the HEPA air filter configured to prevent microbial contamination of the sterile environment inside of the enclosure.

7. The enclosure of claim 1, wherein the fenestration includes an outer seal over a patient-interfacing surface of the patient-interfacing portion of the barrier in the sealed state of the fenestration.

8. The enclosure of claim 7, wherein a perimeter of the patient-interfacing surface of the patient-interfacing portion of the barrier around the fenestration includes an adhesive configured to adhere the patient-interfacing portion of the barrier to the patient with the perimeter of the fenestration around the area of interest subsequent to sterilization thereof, the outer seal of the fenestration configured to protect and maintain an integrity of the adhesive prior to use.

9. The enclosure of claim 7, wherein the fenestration includes an inner seal over an inner surface of the patient-interfacing portion of the barrier in the sealed state of the fenestration, the inner seal of the fenestration configured to be removed subsequent to adhering the patient-interfacing portion of the barrier to the patient, thereby maintaining the sterile environment over the patient.

10. The enclosure of claim 1, further comprising one or more pairs of long-sleeved gloves integrated into the expandable portion of the barrier configured to be worn by a clinician when performing the medical procedure within the sterile environment.

11. The enclosure of claim 1, further comprising one or more closed-ended tubes integrated into the expandable portion of the barrier configured to accept insertion of a probe for use during the medical procedure within the sterile environment.

12. The enclosure of claim 1, further comprising one or more pockets integrated into the expandable portion of the barrier configured to hold procedural equipment or supplies for the medical procedure, the one or more pockets inside of the enclosure, outside of the enclosure, or a combination thereof.

13. The enclosure of claim 1, further comprising an introducing means for introducing additional procedural equipment or supplies into the sterile environment inside of the enclosure from the non-sterile environment outside of the enclosure.

14. A system for establishing a sterile environment over a patient for a medical procedure, comprising:
an enclosure for placement over the patient including:
an expandable portion of a barrier separating the sterile environment inside of the enclosure from a non-sterile environment outside of the enclosure, the expandable portion of the barrier configured to expand from an unexpanded state to an expanded state for working within the sterile environment;
a patient-interfacing portion of the barrier including a fenestration configured for placement directly over an area of interest of the patient, the fenestration having a sealed state and an unsealed state for access to the area of interest from within the sterile environment; and
a support system coupled to the patient-interfacing portion of the barrier flanking the fenestration, the support system configured to support the enclosure on a surface when the patient-interfacing portion is placed over an appendage of the patient or a main body of the patient, the patient positioned on the surface in any one of a number of anatomical positions; and
procedural equipment or supplies for the medical procedure in the sterile environment inside of the enclosure.

15. The system of claim 14, wherein the fenestration includes an outer seal over a patient-interfacing surface of the patient-interfacing portion of the barrier in the sealed state of the fenestration.

16. The system of claim 15, wherein a perimeter of the patient-interfacing surface of the patient-interfacing portion of the barrier around the fenestration includes an adhesive configured to adhere the patient-interfacing portion of the barrier to the patient with the perimeter of the fenestration around the area of interest subsequent to sterilization thereof, the outer seal of the fenestration configured to protect and maintain an integrity of the adhesive prior to use.

17. The system of claim 15, wherein the fenestration includes an inner seal over an inner surface of the patient-interfacing portion of the barrier in the sealed state of the fenestration, the inner seal of the fenestration configured to be removed subsequent to adhering the patient-interfacing portion of the barrier to the patient, thereby maintaining the sterile environment over the patient.

18. The system of claim 14, wherein the procedural equipment includes one or more puncturing devices, one or more guidewires selected from access guidewires, maneuver guidewires, and rail guidewires, one or more catheters, one or more syringes, or a combination thereof.

19. The system of claim 14, wherein the supplies include one or more packages of an antiseptic, saline, or a medicament, one or more swabs, gauze, one or more drapes, or a combination thereof.

20. A method of a system for establishing a sterile environment over a patient for a medical procedure, comprising:
placing an enclosure over an appendage of the patient or a main body of the patient such that a fenestration of a patient-interfacing portion of a barrier of the enclosure is directly over an area of interest of the patient;
expanding an expandable portion of the barrier separating a sterile environment inside of the enclosure from a non-sterile environment outside of the enclosure from an unexpanded state to an expanded state; and
working in the sterile environment to perform the medical procedure,
wherein the enclosure includes a support system coupled to the patient-interfacing portion of the barrier flanking the fenestration, the support system configured to support the enclosure on a surface when:
the patient-interfacing portion is placed over the appendage of the patient or the main body of the patient, and
the patient is positioned on the surface in any one of a number of anatomical positions.

21. The method of claim 20, wherein expanding the expandable portion of the barrier includes lifting each framed end of a pair of framed ends of the enclosure from the patient-interfacing portion of the barrier in the unexpanded state of the expandable portion of the barrier to form the expanded state thereof.

22. The method of claim 20, wherein expanding the expandable portion of the barrier includes introducing filtered air into the inside of the enclosure with an air inlet fluidly connected to the inside of the enclosure.

23. The method of claim 22, wherein introducing the filtered air into the inside of the enclosure with the air inlet also introduces the filtered air into the support system coupled to the patient-interfacing portion of the barrier that flanks both the fenestration and the appendage or main body of the patient, thereby expanding the support system from an unexpanded state to an expanded state in concert with the expandable portion of the barrier.

24. The method of claim 20, further comprising:
removing an outer seal of the fenestration from a patient-interfacing surface of the patient-interfacing portion of the barrier, thereby exposing a perimeter around the fenestration having an adhesive on the patient-interfacing surface; and
adhering the patient-interfacing portion of the barrier to the patient with the perimeter of the fenestration around the area of interest.

25. The method of claim 24, further comprising removing an inner seal of the fenestration from an inner surface of the patient-interfacing portion of the barrier after adhering the patient-interfacing portion of the barrier to the patient, thereby maintaining the sterile environment over the patient.

* * * * *